US00PP15505P2

(12) United States Plant Patent
Berry

(10) Patent No.: US PP15,505 P2
(45) Date of Patent: Jan. 25, 2005

(54) ***CLETHRA ALNIFOLIA* PLANT NAMED 'SOTITE'**

(50) Latin Name: *Clethra alnifolia*
Varietal Denomination: Sotite

(75) Inventor: James Bryan Berry, Daphne, AL (US)

(73) Assignee: Plant Development Services Inc., Loxley, AL (US)

( * ) Notice: Subject to any disclaimer, the term of this patent is extended or adjusted under 35 U.S.C. 154(b) by 25 days.

(21) Appl. No.: 10/370,763
(22) Filed: Feb. 24, 2003
(51) Int. Cl.[7] ..... A01H 5/00
(52) U.S. Cl. ..... Plt./226
(58) Field of Search ..... Plt./226

*Primary Examiner*—Anne Marie Grunberg

(57) ABSTRACT

A new and distinct variety of *Clethra alnifolia* plant which possesses a low compact growth habit, dark green foliage, and an abundance of fragrant white flowers.

2 Drawing Sheets

BACKGROUND OF THE INVENTION

The present invention relates to a new and distinct cultivar of *Clethra,* botanically known as *Clethra alnifolia,* and hereinafter referred to by the cultivar name 'Sotite'. This new *Clethra* variety was discovered by James Bryan Berry in May, 1996 as an openly pollinated seedling of *Clethra alnifolia* 'Hummingbird', an unpatented variety maintained by Plant Development Services Inc. in Loxley, Ala. The value of this new cultivar lies in its unique low compact growth habit, dark green foliage, and abundance of fragrant white flowers. 'Sotite' has retained many of the outstanding attributes of the parent cultivar, in particular its tolerance of heat, drought, insects, and diseases which makes it adaptable to culture in the Sunbelt states.

Asexual propagation of the new plant by cuttings has been under Mr. Berry's direction at the same location. The new plant retains its distinctive characteristics and reproduces true to the type in successive generations. The plant cannot be reproduced true from seed.

SUMMARY OF THE INVENTION

The following are the most outstanding and distinguishing characteristics of this new cultivar when grown under normal horticultural practices in Loxley, Ala.

1. Low, compact growth habit.
2. Bright yellow-green immature foliage in the spring matures to a dark green and finally to an attractive yellow fall color.
3. Produces an abundance of attractive fragrant white flowers in the summer.
4. Easily propagated with semi-hardwood cuttings in late spring through the summer.
5. Medium to fast growth rate under normal fertilization and moisture conditions.
6. Performs well in sun or shade.
7. Ideal for mass plantings and low hedges.
8. Good specimen plant.
9. Tolerates moist or dry soil.
10. Relatively pest resistant.
11. Hardy to Zone 3.
12. Attracts butterflies.
13. Good plant for coastal areas due to wind and salt tolerance.

DESCRIPTION OF THE DRAWING

This new *Clethra alnifolia* variety is illustrated by the accompanying photographic prints in which:

1. The photograph at the top of the first sheet is a close-up view showing flower, foliage, and stem color as well as flower form of the new variety in mid-summer.

2. The photograph at the bottom of the first sheet shows the low compact growth habit, dark green foliage, and the abundance of white flowers of the new variety grown in a seven gallon container.

3. The photograph on the second sheet is a side-by-side comparison of (from left to right) 'Sotite', *Clethra alnifolia* 'Hummingbird', and *Clethra alnifolia* 'September Beauty' U.S. Plant Pat. No. 10,481. This photograph, which was taken in mid-summer, shows the low compact growth habit, dark green foliage, and the abundance of upright terminal racemes of the new variety grown in a three gallon container.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of *Clethra* based on my observations made of 2 year old plants grown in 3 gallon containers in wholesale commercial production practices, in greenhouses, and in established landscape plantings in Loxley, Ala.

DISTINCTIVE CHARACTERISTICS

| Characteristic | *Clethra alnifolia* 'Sotite' | *Clethra alnifolia* 'Hummingbird' | *Clethra alnifolia* 'September Beauty' PP# 10.481 |
|---|---|---|---|
| Height (Mature) | 2–3' | 3–4' | 6–7' |
| Width (Mature) | 3–4' | 3–4' | 3–4' |
| Growth Habit | Low Compact | Low Compact | Upright Compact |
| Leaf Length | 1¼–2¾" | 1–2½" | 3–3½" |
| Leaf Width | ¾–1½" | 1–1½" | 1¼–1 9/16" |
| Bloom Time | June–July | June–July | July–August |
| Raceme Length | 3–4" | 4–6" | 4–6" |

*Clethra* 'Sotite' is similar to the two cultivars listed above, however, in side-by-side comparisons conducted in Loxley, Ala., 'Sotite' produced a smaller, more compact plant that begins blooming seven to ten days after 'Hummingbird' and ten to fourteen days before 'September Beauty'. The new variety is sold under the trade name White Dove and is listed as *Clethra alnifolia* White Dove™ 'Sotite'.

Classification

Botanical: *Clethra alnifolia* 'Sotite'

Parentage: Openly pollinated seedling of *Clethra alnifolia* 'Hummingbird'

Commercial: Deciduous shrub.

Form: Low and compact.

Height: 2–3'.

Width: 3–4'.

Growth Rate: Medium to fast under normal fertilization and moisture conditions. Mature height is 2–3' and width 3–4'. This varies from the parent cultivar which has a 3–4' mature height. Rooted cuttings can be produced in 2–3 months when propagated in late spring in Loxley, Ala. Root development is vigorous and finely branched. From a rooted cutting, the new variety reaches a height of 2' and a spread of 3' in a period of four years. Under normal growing conditions in Loxley, Ala., the growth rate is normally about 4–6" per year while maintaining a dense habit due to the abundant branch development and short internode lengths.

Foliage: Alternate, flat, simple, obovate, deciduous, 1¼ to 2¾" long and ¾ to 1½" wide. Apex is acute to short acuminate; the base is cuneate; the margins are sharply serrate and usually entire toward base. The petioles are ⅛ to ⅜" long, 1/16" in diameter, pubescent, and Yellow-Green Group 147D maturing to Yellow-Green 147C. Leaf venation is pinnate. Mid-veins and laterals are pubescent, impressed on the upper leaf surface and prominent on the underside. Immature mid and lateral veins are Yellow-Green Group 147D top and bottom and mature to Yellow-Green Group 147C. The upper surface of the immature leaf is glossy, glabrous, and Yellow-Green Group 144B. The lower surface of the immature leaf is Yellow-Green Group 144C and matte. As the leaves mature the upper surface becomes closest to Green Group 137A and the lower leaf surface becomes Green Group 137D. With the onset of cool weather in the fall, the leaf color changes to Yellow Group 13A and finally Greyed-Orange Group 165A just before falling.

In 1999, the date of initial spring growth was March 20, in Loxley, Ala. After the initial spring flush, there was almost continuous growth until fall, ending October 8, also in Loxley, Ala. This growth pattern was identical to the parent cultivar. When grown in full sun, the internode length of 'Sotite' is 3/16" to ½" compared to ⅜ to ⅝" for the parent cultivar. When grown in light shade, the internode length is 5/16" to ¾" for 'Sotite' and ½ to ⅞" for the parent cultivar. As would be expected, either plant grown in the shade results in a taller, less dense plant with larger leaves.

Stems: The young shoots are Yellow-Green Group 147D, pubescent and matte. In about a month this color changes to Yellow-Green Group 147C and by the fall the stem color is Greyed-Orange Group 177B. After one or more years, the stems are generally Greyed-Orange Group 177A, glabrous and rugose. The plant is densely branched throughout the entire shrub. The pith is solid and uniform.

Flowers: Perfect, fragrant, produced in dense, pubescent, upright terminal racemes or panicles on current season's growth. The pedicel is ⅛ to ⅜" long and Yellow-Green Group 147D becoming Yellow-Green Group 145C as the flowers open. Each pedicel has a pair of bracts which are ⅛ to ¼" long and Yellow-Green Group 147D. As the flowers open the bracts quickly change to Brown Group 200D and fall off. The inflorescence is indeterminate. The distal immature buds are ovate, 1/16 to ⅛" long, 1/32 to 1/16" wide, and Yellow-Green Group 147D. As the buds open they are ovate, ⅛ to 3/16" long, 1/16" to ⅛" wide, and Yellow-Green Group 145C. Flowers are ⅜" long, ⅜" in diameter and White Group 155C front and back. Each flower has five petals that are 3/16 to 5/16" long and 1/16 to ⅛" wide, ovate and have obtuse tips. The five ovate shaped sepals are joined at the base, ⅛ to 3/16" long, 1/16" wide, have acute tips and are Yellow-Green Group 145C. The ten stamens are ¼ to 5/16" long. The filaments are White Group 155C. The anthers are 1/16" long, Yellow-Orange Group 18A, and quickly mature to Greyed-Orange Group 172B. The mature pollen is Yellow Group 11D. The pistil is single, slender styled, and 3-cleft. The style is White Group 155C and ⅛ to 3/16" long. The ovary is Yellow-Green Group 145C and inferior.

Flowers are borne on terminal racemes or panicles which are Yellow-Green Group 148C at the base and Yellow-Green Group 145D distally. The diameter of the peduncle is ⅛ to 3/16" at the base tapering to 1/16" at the apex. Each raceme is 3 to 4" long and 1 to 1¼" wide. There are 1 to 6 racemes per stem. The main racemes have 70–80 flowers and the side racemes have 30–50 flowers. A mature plant may have several hundred racemes producing several thousand flowers. There is a four to six week flowering period normally beginning in Mid-June in Loxley, Ala. The date of full bloom was July 10 in 1999 in Loxley, Ala. Individual blooms last on the plant in the garden three to five days. Flowers have a spicy fragrance.

Fruit: Dry, three-valved, dehiscent, pubescent, subglobose, ⅛" diameter capsule. The capsule matures from Yellow-Green Group 148C in the summer to Green Group 137D in the fall and persists as Greyed-Green Group 197A attractively through the winter. The capsule opens in the fall to release the 8–12 glabrous seeds which are 1/16" in diameter, flat, and Greyed-Orange Group 166B. Normal fruit set is heavy.

Culture: Grows well in a wide range of conditions and tolerates sun to shade. Prefers a moist, well-drained soil that is rich in organic matter. Responds well to mulching and medium applications of fertilizer; prefers ph 5.0 to 5.5. Very little pruning is needed; adaptable to container and above ground planters. Tolerates wind and salt of the seashore. Cold hardiness and drought resistance is comparable to the parent cultivar.

Disease and insect resistance: Resistance to diseases and insects common to plants of *Clethra* has not been observed.

I claim:

1. A new and unique variety of *Clethra alnifolia* plant named 'Sotite' as herein shown and described.

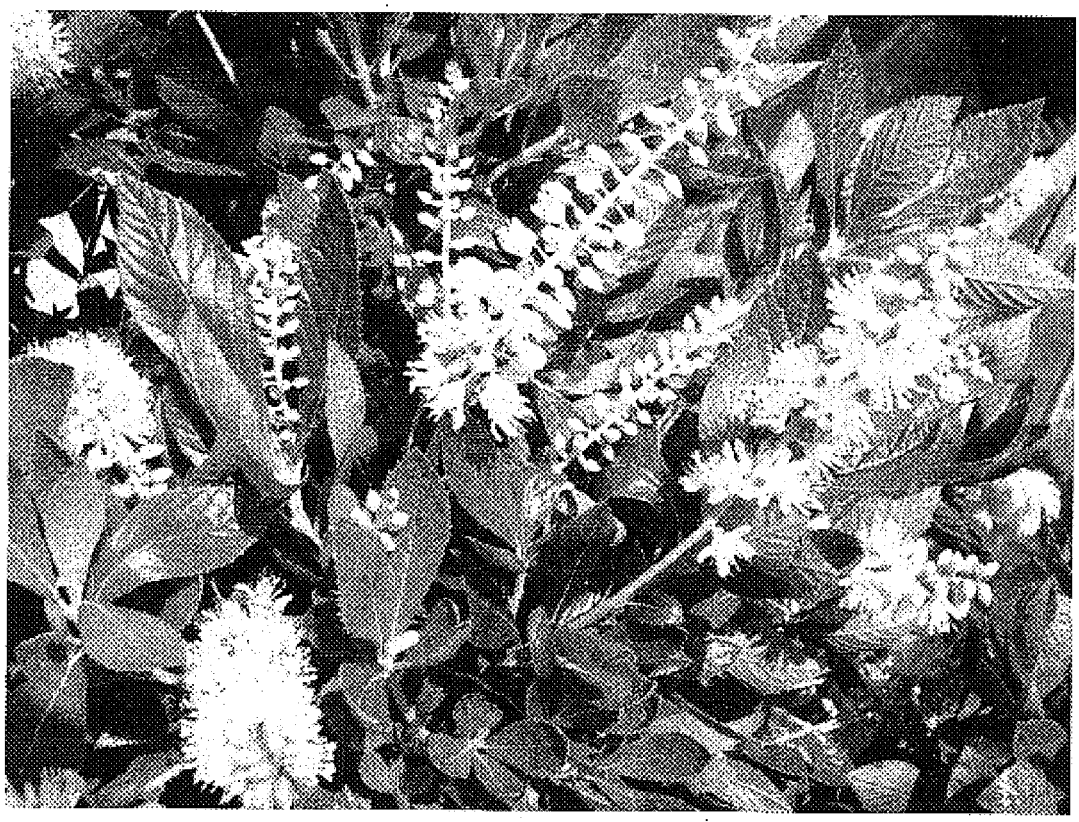
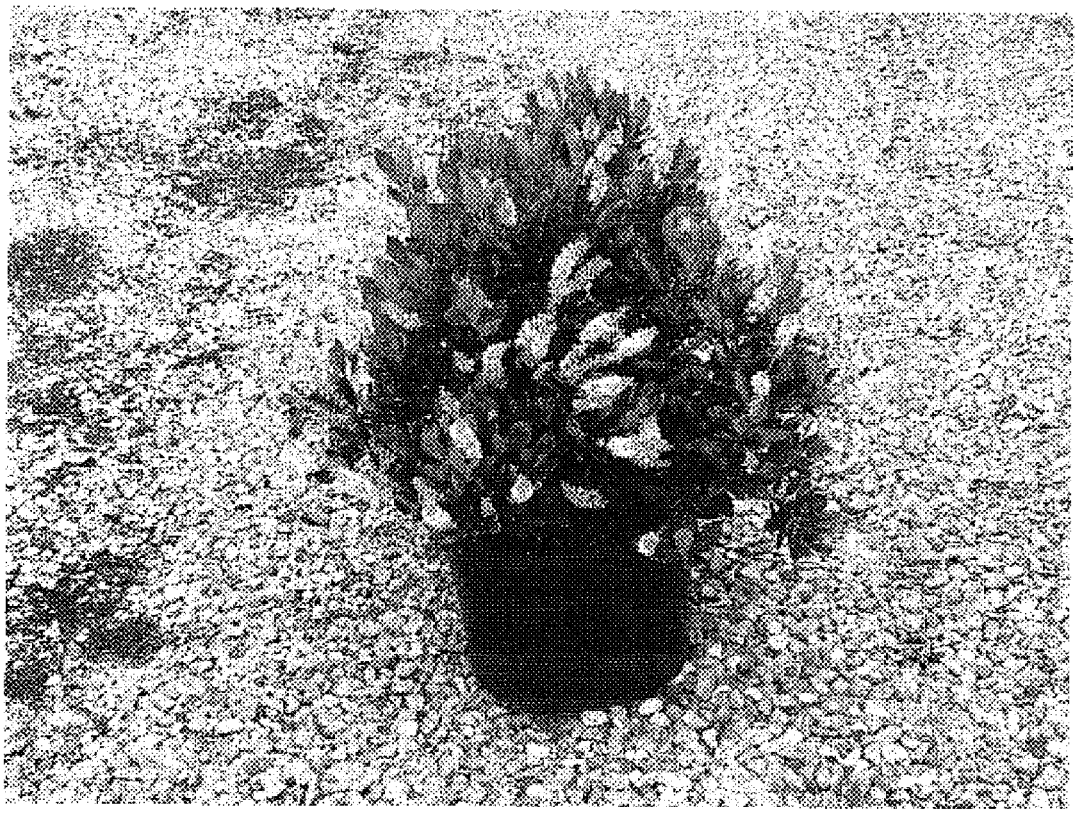

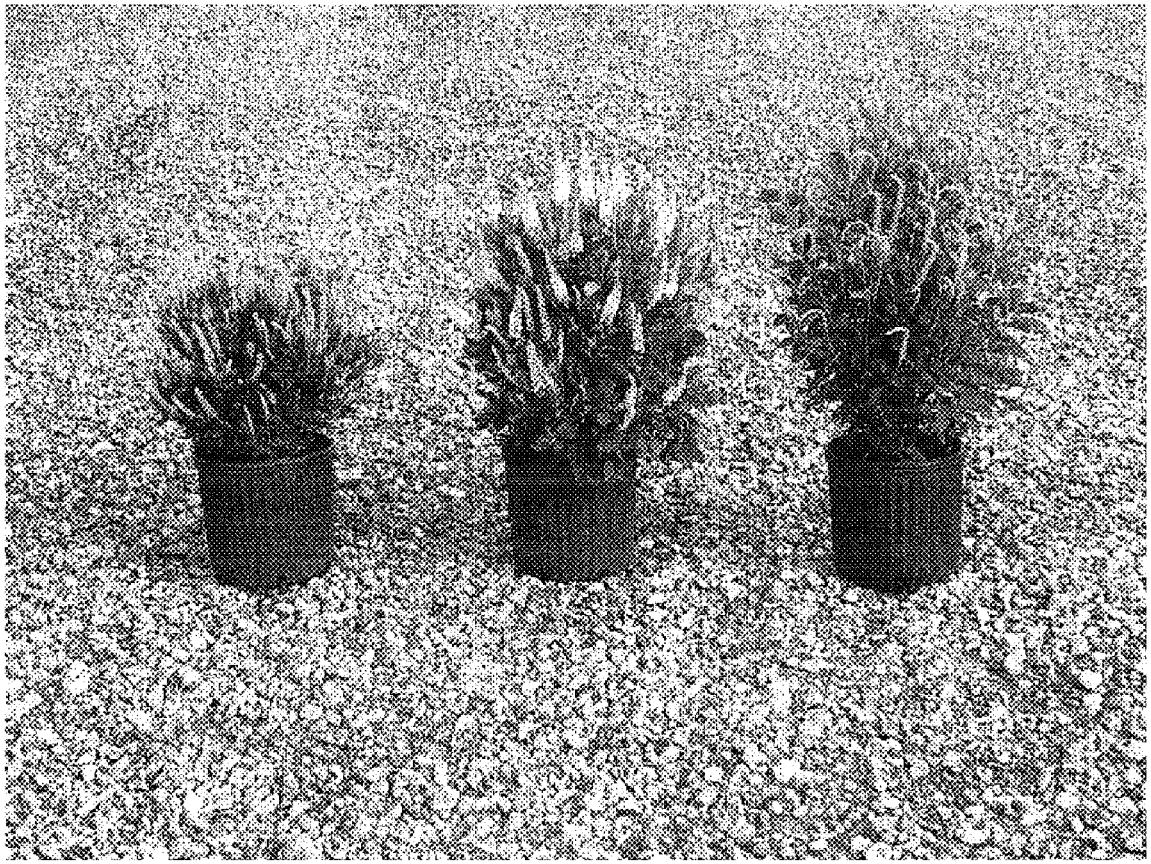

* * * * *